US009840540B2

(12) United States Patent
Tanaka

(10) Patent No.: US 9,840,540 B2
(45) Date of Patent: Dec. 12, 2017

(54) ARTIFICIAL BIOPARTICLE AND METHOD OF MANUFACTURING THE SAME

(71) Applicant: JAPAN SCIENCE AND TECHNOLOGY AGENCY, Kawaguchi-shi, Saitama (JP)

(72) Inventor: Hideaki Tanaka, Suita (JP)

(73) Assignee: Japan Science and Technology Agency, Kawaguchi (JP)

( * ) Notice: Subject to any disclaimer, the term of this patent is extended or adjusted under 35 U.S.C. 154(b) by 0 days.

(21) Appl. No.: 14/443,503

(22) PCT Filed: Nov. 8, 2013

(86) PCT No.: PCT/JP2013/080219
§ 371 (c)(1),
(2) Date: May 18, 2015

(87) PCT Pub. No.: WO2014/077195
PCT Pub. Date: May 22, 2014

(65) Prior Publication Data
US 2016/0002305 A1    Jan. 7, 2016

(30) Foreign Application Priority Data
Nov. 19, 2012   (JP) .................. 2012-253031

(51) Int. Cl.
| C07K 1/00 | (2006.01) |
| C07K 14/00 | (2006.01) |
| C07K 17/00 | (2006.01) |
| C07K 14/47 | (2006.01) |
| C12N 15/90 | (2006.01) |

(52) U.S. Cl.
CPC ............ *C07K 14/47* (2013.01); *C12N 15/902* (2013.01); *C07K 2319/73* (2013.01)

(58) Field of Classification Search
None
See application file for complete search history.

(56) References Cited

U.S. PATENT DOCUMENTS

| 2002/0055627 A1 | 5/2002 | Rosen et al. |
| 2009/0238822 A1 | 9/2009 | George et al. |
| 2011/0059502 A1 | 3/2011 | Chalasani |
| 2011/0201112 A1 | 8/2011 | Rome et al. |

FOREIGN PATENT DOCUMENTS

| JP | 2002-516675 A | 6/2002 |
| JP | 2007-508846 A | 4/2007 |
| JP | 2009-511024 A | 3/2009 |
| JP | 2013-509202 A | 3/2013 |
| WO | WO 1999/062547 A1 | 12/1999 |
| WO | WO 2003/020906 A2 | 3/2003 |
| WO | WO 2004/081533 A2 | 9/2004 |
| WO | WO 2005/056752 A2 | 6/2005 |
| WO | WO 2011/053991 A2 | 5/2011 |

OTHER PUBLICATIONS

Han et al. "Targeted Vault Nanoparticles Engineered with an Endosomolytic Peptide Deliver Biomolecules to the Cytoplasm" ACS Nano 5:6128-6137. Published Jul. 9, 2011.*
Mirksovsak and Larsen "pH Induced Secondary Structure Formation: Experimental Desing of a GCN4-p1 Sequence", p. 182, in Methods in Protein Structure and Stability Analysis Part C. Conformational Stability, Size, Shape and Surface of Protein Molecules, edited by V. Uversky and E. Permyakov. 2007.*
Chen et al. "Fusion protein linkers: Property, design and functionality" Advanced Drug Delivery Reviews 65:1357-1369. Published online Sep. 29, 2012.*
Han et al. "Targeted Vault Nanoparticles Engineered with an Endosomolytic Peptide Deliver Biomolecules to the Cytoplasm" ACS Nano 5:6128-6137. Published online Jul. 9, 2011.*
Miksovska and Larsen "pH Induced Secondary Structure Formation: Experimental Design of a GCN4-p1 Sequence" from Methods of Protein Structure and Stability Analysis Part C. Conformational Stability, Size, Shape and Surface of Protein Molecules. Edited by V. Uversky and E. Permyakov. p. 182. Published 2007.*
Han et al., *ACS Nano*, 5(8): 6128-6137 (2011).
Kickhoefer et al., *PNAS*, 102(12): 4348-4352 (2005).
Kickhoefer et al., *ACS Nano*, 3(1): 27-36 [doi: 10.1021/nn800638x] (Jan. 27, 2009).
Stephen et al., *The Journal of Biological Chemistry*, 276(26): 23217-23220 (2001).
Tanaka et al., *Science*, 323: 384-388 (2009).
Yu et al., *Nano Letters*, 8(10): 3510-3515 (2008).
Japanese Patent Office, International Search Report in International Patent Application No. PCT/JP2013/080219 (dated Feb. 4, 2014).
Mikyas et al., *J. Mol. Biol.*, 344: 91-105 (2004).
Chinese Patent Office, The First Office Action in Chinese Patent Application No. 201380060146.9 (dated May 25, 2016).
European Patent Office, Supplementary European Search Report in European Patent Application No. 13855679 (dated May 4, 2016).
Patterson, Dustin P., "Symmetry Assembled Supramolecular Protein Cages: Investigating a Strategy for Constructing New Biomaterials," Dissertation Submitted in Partial Fulfillment of the Requirements for the Degree of Doctor of Philosophy (Chemistry) in The University of Michigan, pp. 1-170 (2011).

(Continued)

*Primary Examiner* — Christina Bradley
*Assistant Examiner* — Zachary J Miknis
(74) *Attorney, Agent, or Firm* — Leydig, Voit & Mayer, Ltd.

(57) ABSTRACT

According to an artificial bioparticle characterized in that a leucine zipper is integrated in each N terminal of an MVP constituting a waist of a vault and a method of manufacturing an artificial bioparticle in which a leucine zipper gene is integrated and expressed in a side to be an N terminal of an MVP gene, a novel artificial bioparticle including a vault of which large internal space can effectively be made use of, which can be used as a nanocapsule applicable to a drug delivery system (DDS), and a method of manufacturing the same are provided.

5 Claims, 4 Drawing Sheets

(56) References Cited

OTHER PUBLICATIONS

Korean Patent Office, Office Action in Korean Patent Application No. 10-2015-7014295 (dated Jul. 13, 2016).
Korean Patent Office, Decision for Grant of Patent in Korean Patent Application No. 2015-7014295 (dated Sep. 5, 2016).

* cited by examiner

ARTIFICIAL BIOPARTICLE AND METHOD OF MANUFACTURING THE SAME

CROSS-REFERENCE TO RELATED APPLICATIONS

This patent application is the U.S. national phase of International Patent Application No. PCT/JP2013/080219, filed Nov. 8, 2013, which claims the benefit of Japanese Patent Application No. 2012-253031, filed on Nov. 19, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 42,877 bytes ASCII (Text) file named "720653Replacement-SequenceListing.txt," created Aug. 25, 2015.

TECHNICAL FIELD

The present invention relates to a novel artificial bioparticle including a vault, which can be used as a nanocapsule applicable to a drug delivery system (DDS), and a method of manufacturing the same.

BACKGROUND ART

A vault 2 is a huge ovoid bioparticle having a particle size of 40 nm×40 nm×67 nm, and it is a nucleic acid-protein complex having a largest molecular weight within a cell (see FIG. 2). Vault 2 present in an organism is constituted of three types of proteins (major vault protein (MVP), vault poly(ADP-ribose)polymerase (VPARP), and telomerase-associated protein-1 (TEP1)) and one type of RNA. Vault 2 is such that 39 MVPs 3, which are main components and have a molecular weight of approximately 100 kDa, gather to form a half vault in a shape of a bowl (each site being referred to as a cap 5, a shoulder 6, a body 7, and a waist 8) and two halves are associated at waist 8 as if edges of the bowls were coupled, to thereby form an outer shell of the ovoid particle. Components other than the MVP are present in an internal space formed by the outer shell.

MVP 3 forming the outer shell of vault 2 is constituted of 12 domains in total including 9 repeating structures (3a, 3b, 3c, 3d, 3e, 3f, 3g, 3h, 3i) formed from antiparallel β sheets and shoulder 6, a cap helix 9, and a cap ring 10 (FIG. 3), and intermolecular hydrophobic bond between domains of cap helix 9 is important for formation of a half vault in a bowl shape. Two half vaults form the ovoid vault particle by associating N terminals of MVPs 3, and such association is formed only based on very weak interaction of ionic bond and a short intermolecular β sheet. Such structural information of the vault and a mechanism of formation of a particle have been clarified as the present inventor succeeded in overall structure determination of a rat liver derived vault in 2009 (see, for example, Hideaki Tanaka et al., "The Structure of Rat Liver Vault at 3.5 Angstrom Resolution," Science, Vol. 323, pp. 384-388 (2009) (NPD 1)).

It has previously been known that as an MVP which is a main component of a vault is expressed in an insect cell, an ovoid particle the same as in an organism is formed (see, for example, Andrew G. Stephen et al., "Assembly of Vault-like Particles in Insect Cells Expressing Only the Major Vault Protein," The Journal of Biological Chemistry, Vol. 276, No. 26, pp. 23217-23220 (2001) (NPD 2)). Owing to a characteristic shape of a vault, development of a drug delivery system (DDS) by using the vault as a nanocapsule has progressed (see, for example, Valerie A. Kickhoefer et al., "Engineering of vault nanocapsules with enzymatic and fluorescent properties," PNAS, Vol. 102, No. 12, pp. 4348-4352 (2005) (NPD 3) and Valerie A. Kickhoefer et al., "Targeting Vault Nanoparticles to Specific Cell Surface Receptors," ACS nano, 3 (1): 27-36.doi: 10.1021/nn800638x(2009) (NPD 4)).

For example, Japanese National Patent Publication No. 2013-509202 (PTD 1) has disclosed use of a vault particle which is a recombinant particle having an MVP as well as a fusion protein and mINT and a protein of interest (cytokine) for delivery of the protein of interest to a cell or a tumor, or a target. In addition, for example, Japanese National Patent Publication No. 2007-508846 (PTD 2) has disclosed a technique directed to a composition for delivering a polynucleotide packaged by a polypeptide, having a leucine zipper as a polynucleotide-bound domain.

In a conventional method, for taking a drug into a particle, a C terminal 160 residue (an INT domain: bonding to an MVP) of a VPARP which is a constituent component of a vault and present in a particle is used as a tag. Such use is also for having the particle retain the drug therein. This method, however, has not yet successfully made full use of a large internal space in the vault.

CITATION LIST

Patent Document

PTD 1: Japanese National Patent Publication No. 2013-509202
PTD 2: Japanese National Patent Publication No. 2007-508846

Non Patent Document

NPD 1: Hideaki Tanaka et al., "The Structure of Rat Liver Vault at 3.5 Angstrom Resolution," Science, Vol. 323, pp. 384-388 (2009)
NPD 2: Andrew G. Stephen et al., "Assembly of Vault-like Particles in Insect Cells Expressing Only the Major Vault Protein," The Journal of Biological Chemistry, Vol. 276, No. 26, pp. 23217-23220 (2001)
NPD 3: Valerie A. Kickhoefer et al., "Engineering of vault nanocapsules with enzymatic and fluorescent properties," PNAS, Vol. 102, No. 12, pp. 4348-4352 (2005)
NPD 4: Valerie A. Kickhoefer et al., "Targeting Vault Nanoparticles to Specific Cell Surface Receptors," ACS nano, 3 (1): 27-36.doi: 10.1021/nn800638x(2009)

SUMMARY OF INVENTION

Technical Problem

The present invention was made to solve the problems above, and an object thereof is to provide a novel artificial bioparticle including a vault of which large internal space can effectively be made use of, which can be used as a nanocapsule applicable to a drug delivery system (DDS), and a method of manufacturing the same.

Solution to Problem

An artificial bioparticle according to the present invention is characterized in that a leucine zipper is integrated in each N terminal of an MVP constituting a waist of a vault.

In the artificial bioparticle according to the present invention, preferably, a linker is interposed between the N terminal of the MVP and the leucine zipper. In this case, preferably, the linker includes 3 to 6 glycines.

In the artificial bioparticle according to the present invention, preferably, the leucine zipper is derived from GCN4 which is a transcription activator factor of yeast.

The present invention also provides a method of manufacturing the artificial bioparticle according to the present invention described above, which includes integrating and expressing a leucine zipper gene in a side of an MVP gene, which is to be an N terminal.

In the method of manufacturing the artificial bioparticle according to the present invention, the MVP gene and the leucine zipper gene are coupled by a gene encoding a linker, without a restriction enzyme site being interposed.

Advantageous Effects of Invention

According to the method of manufacturing an artificial bioparticle in the present invention, an artificial bioparticle can be obtained at yields remarkably higher than in a conventional example. The artificial bioparticle according to the present invention is expected as a nanocapsule which can be used for a DDS and of which internal space can effectively be made use of, and according to the present invention, yields are higher by an order of magnitude, which leads to significant reduction in cost. Based on the artificial bioparticle according to the present invention, progress in development of a particle of which opening and closing can reversibly be controlled depending on pH can be expected.

DESCRIPTION OF EMBODIMENTS

Figure 1:
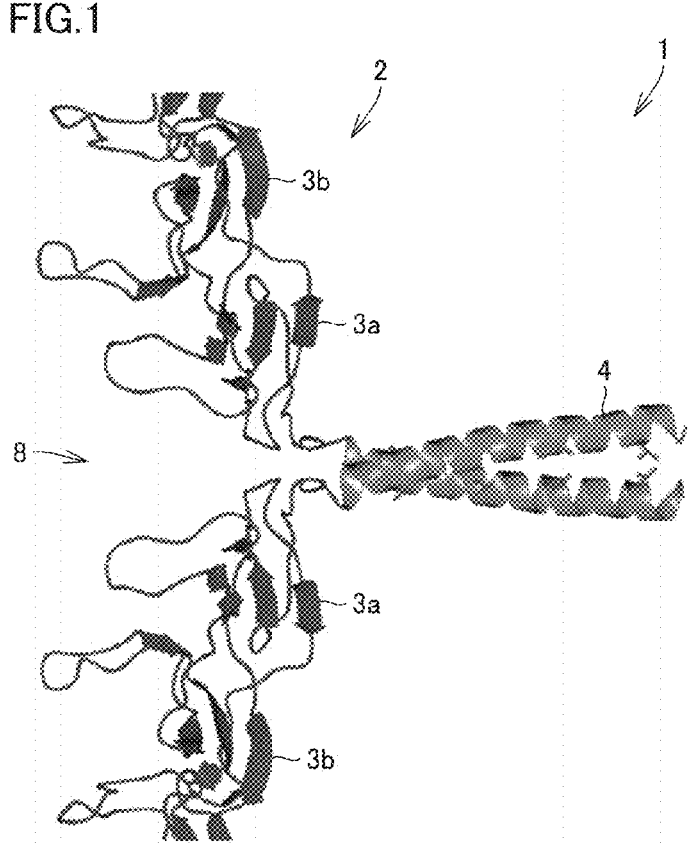
FIG. 1 is a schematic diagram conceptually showing bond between an N terminal 3a of an MVP 3 constituting a vault 2 and a leucine zipper 4 in an artificial bioparticle 1 according to the present invention.
Figure 2:
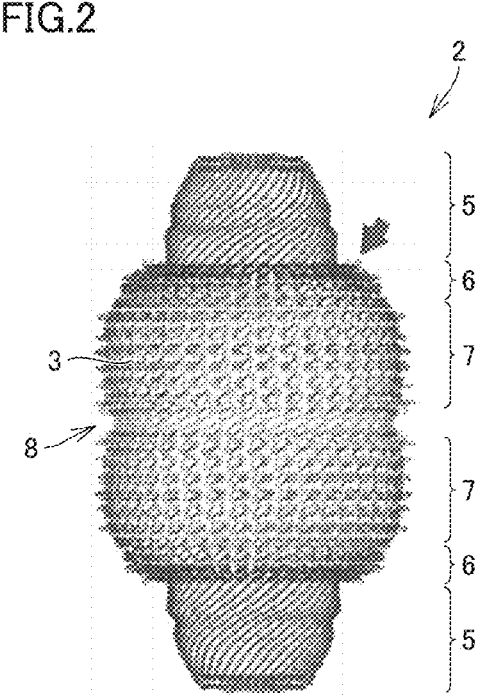
FIG. 2 is a diagram schematically showing vault 2 used for artificial bioparticle 1 according to the present invention.
Figure 3:
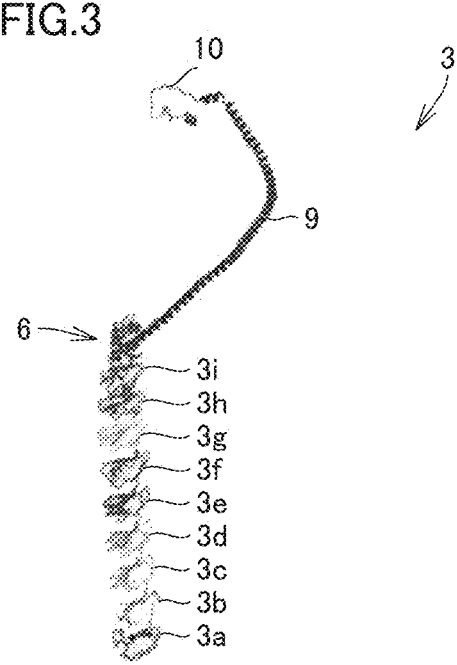
FIG. 3 is a diagram schematically showing MVP 3 constituting vault 2.

FIG. 1 is a schematic diagram conceptually showing bond between an N terminal 3a of MVP 3 constituting vault 2 and leucine zipper 4 in an artificial bioparticle 1 according to the present invention. FIG. 2 is a diagram schematically showing vault 2 used for artificial bioparticle 1 according to the present invention and FIG. 3 is a diagram schematically showing MVP 3 constituting vault 2. As described above, vault 2 is such that 39 MVPs 3 representing main components gather to form a half vault in a shape of a bowl (each site being referred to as cap 5, shoulder 6, body 7, and waist 8) and two halves are associated at waist 8 as if edges of the bowls were coupled, to thereby form an outer shell of the ovoid particle (FIG. 2). MVP 3 forming the outer shell of vault 2 is constituted of 12 domains in total including 9 repeating structures (3a, 3b, 3c, 3d, 3e, 3f, 3g, 3h, 3i) formed from antiparallel β sheets and shoulder 6, cap helix 9, and cap ring 10 (FIG. 3). Artificial bioparticle 1 according to the present invention is characterized in that leucine zipper 4 is integrated in each N terminal of MVP 3 constituting waist 8 of vault 2.

In artificial bioparticle 1 according to the present invention, a linker is preferably interposed between the N terminal of MVP 3 and leucine zipper 4. As such a linker is interposed, a degree of freedom of movement of leucine zipper 4 in artificial bioparticle 1 is ensured.

The linker between the N terminal of MVP 3 and leucine zipper 4 in artificial bioparticle 1 according to the present invention is preferably formed from 1 to 6 small amino acid(s) aligned in a straight chain. Though artificial bioparticle 1 having leucine zipper 4 is expressed in any case of 1 to 6 amino acids forming the linker, from a point of view of uniformity in obtained artificial bioparticles 1 and a greater amount of expression and from a point of view of a degree of freedom of movement of leucine zipper 4, the linker is preferably formed from 3 to 6 small amino acids as aligned in a straight chain. The amino acid constituting the linker is exemplified by an amino acid having a small side chain such as glycine or alanine. In a present experimental example which will be described later, an example in which a linker is formed from 3 or 6 straight-chain glycines is shown.

Leucine zipper 4 is a motif like a zipper formed in such a manner that two α-helices each composed of approximately 30 amino acid residues establish hydrophobic bond at leucine residues thereof. For leucine zipper 4 in the present invention, for example, a leucine zipper derived from GCN4 which is a transcription activator factor of yeast or other leucine zippers derived from other proteins can be used without particularly being restricted. Among those, an X-ray crystal structure of a leucine zipper derived from GCN4 which is a transcription activator factor of yeast was determined in 1991 at 1.8 Å resolution, and it was clarified on an atomic level that peptides each constituted of 33 amino acid residues establish hydrophobic bond at leucine residues thereof to thereby form a strong coiled coil. Therefore, a leucine zipper derived from GCN4 which is a transcription activator factor of yeast can suitably be employed.

Such an artificial bioparticle according to the present invention is expected as a nanocapsule of which internal space can effectively be made use of and which can be made use of for a DDS, and according to the present invention, yields are higher by an order of magnitude, which leads to significant reduction in cost. Based on the artificial bioparticle according to the present invention, progress of development of a particle of which opening and closing can reversibly be controlled depending on pH can be expected.

Figure 4:
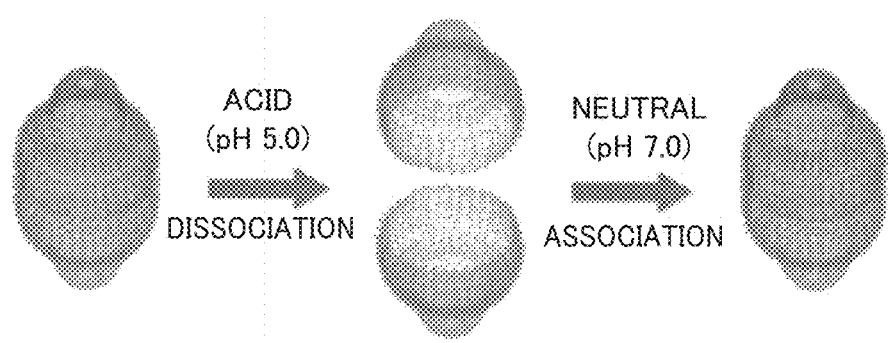
FIG. 4 is a diagram schematically showing application of artificial bioparticle 1 according to the present invention as a nanocapsule.
Figure 5:
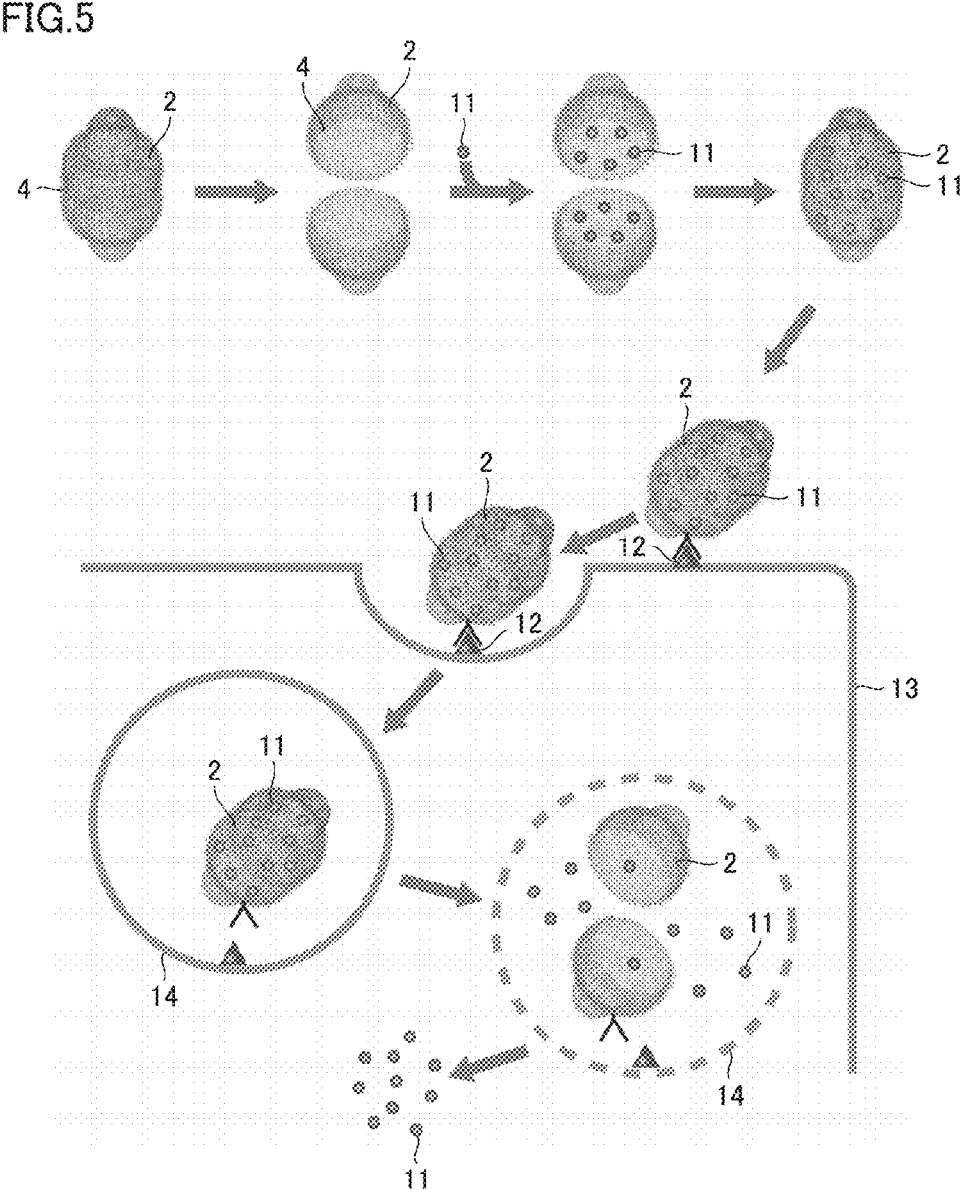
FIG. 5 is a diagram schematically showing one example of a drug delivery system in which artificial bioparticle 1 according to the present invention is applied as a nanocapsule.

Here, FIG. 4 is a diagram schematically showing application of artificial bioparticle 1 according to the present invention as a nanocapsule and FIG. 5 is a diagram schematically showing one example of a DDS in which artificial bioparticle 1 according to the present invention is applied as a nanocapsule. According to artificial bioparticle 1 in the present invention, for example, by introducing a cysteine residue in a leucine zipper attached to an N terminal of an MVP, as shown in FIG. 4, a nanocapsule of which opening and closing can reversibly be controlled depending on pH in such a manner that a stable ovoid particle is formed based on disulfide bond under a neutral condition and the particle opens as if an egg were just split into two as a result of cleavage of disulfide bond under an acid condition can be developed. By using such a nanocapsule, for example, as shown in FIG. 5, such a DDS is also possible that a drug 11 is placed in an internal space of vault 2 under the acid condition followed by administration so that the nanocapsule is taken into a target cell 13 as a result of an antigen-antibody reaction between a specific antigen 12 on a surface of target cell 13 and an antibody (Fab) attached in advance to the surface of vault 2, the nanocapsule opens as an acid condition is established in endosome 14, and drug 11 is released. Such an artificial bioparticle according to the present invention has a very large space therein, and hence it is considered to be viable as a carrier in a gene therapy.

In addition, use of artificial bioparticle 1 according to the present invention as a nanocapsule in which cosmetic components are confined for permeation deep into skin is also possible.

Recently, such a technique has also been established that an internal space of a protein complex is used as a template, a metal is polymerized, and the polymerized product is regularly sequenced so that a substrate serving as a base for an extremely small semiconductor. Though a spherical protein such as ferritin is currently used, by using an oval particle like vault 2 by making use of artificial bioparticle 1 according to the present invention, a novel, unprecedented substrate may be made.

The present invention also provides a method of manufacturing artificial bioparticle 1 characterized in that a leucine zipper gene is integrated and expressed in a side of an MVP gene, which is to be an N terminal. Thus, as will be described later in the experimental example, artificial bioparticle 1 according to the present invention can be obtained at yields significantly higher than, or at least 10 times as high as, in a conventional expression system in which an insect cell having a W-vault formed of wild type MVPs (W-MVP) is employed. Base sequences of the leucine zipper gene and the MVP gene have already been known, and by combining as appropriate conventionally known genetic engineering techniques, a leucine zipper gene can be integrated in a side of an MVP gene which is to be an N terminal. In the experimental example which will be described later, an example in which a fragment of a leucine zipper gene cut from GCN4 which is a transcription activator factor of yeast and purified and a fragment of a rat derived MVP gene similarly cut and purified are ligated (through a linker which will be described later) is shown.

Though a cell, in which a product obtained by integrating a leucine zipper gene in a side of an MVP gene which is to be an N terminal is expressed, is not particularly restricted, an insect cell or a cell of higher forms of life than an insect cell is exemplified. It has been known that a bioparticle is not successfully formed in some cases, for example, when *Escherichia coli* lower than an insect cell is used, and expression by using an insect cell normally used in the field of the art is preferred. SD is exemplified as a specific example of an insect cell. An expressed artificial bioparticle can be purified with a conventionally known appropriate method.

In the method of manufacturing artificial bioparticle 1 according to the present invention, the MVP gene and the leucine zipper gene are coupled by a gene encoding a linker, without a restriction enzyme site being interposed. When a fragment of the leucine zipper gene derived from GCN4 which is a transcription activator factor of yeast and the rat derived MVP gene described above are used, in an attempt for coupling, a site of Ecoki (GAATTC) remains therebetween, which may inhibit formation of a vault particle. In the experimental example which will be described later, an Ecoki site was substituted with a Gly linker which was a series of 3 residues or 6 residues of glycines which were amino acids having a smallest side chain, and thereafter expression in an insect cell was carried out. Specifically, a primer is designed in accordance with a linker to be introduced, and after PCR, the purified fragment is desirably ligated such that it is interposed between an N terminal of an MVP gene and a leucine zipper gene.

In the method of manufacturing artificial bioparticle 1 according to the present invention as well, what is preferred as a leucine zipper or a linker is as described above with regard to artificial bioparticle 1.

Though the present invention will be described in further detail with reference to an experimental example, the present invention is not limited thereto.

EXPERIMENTAL EXAMPLE

[1] Construction of Abundant Expression System of Wild-Type MVP (W-MVP) Using Insect Cell Sf9

[A] Preparation of W-MVP Cloned Recombinant Baculovirus Genome (Bacmid DNA)

An operation was performed in a procedure below.

(1) A DNA of a rat liver derived MVP (W-MVP) was introduced into a pFastBac vector by using a restriction enzyme site of EcoRI and SphI.

(2) Obtained pFastBac was transformed to *Escherichia coli* (DH5α), and the resultant product was placed on an LB plate containing Ampicillin (100 μg/mL) and subjected to standing culture at 37° C. for 24 hours.

(3) Several colonies were picked up with a platinum loop and whether or not a target gene was amplified was observed with colony PCR.

(4) The colony in which amplification of the gene was observed in (3) above was inoculated in 5 mL of an LB liquid culture medium containing Ampicillin (100 μg/mL), and subjected to shake culture at 37° C. overnight.

(5) W-MVP cloned pFastBac was purified from *Escherichia coli* (DH5α) cultured overnight, with QIAprep Spin Miniprep Kit of QIAGEN.

(6) To twenty microliters of DH10Bac, 0.1 μg of W-MVP cloned pFastBac was added and lightly mixed, and thereafter the mixture was rested on ice for 20 minutes.

(7) Heat shock at 42° C. for 1 minute was provided, followed by resting on ice for 2 minutes. Thereafter, 200 μL of an SOC culture medium was added, and the resultant product was subjected to shake culture at 37° C. for 4 hours.

(8) Twenty microliters of the culture solution in (7) above were poured over an LB plate containing kanamycin (50 μg/mL), gentamicin (7 μg/mL), tetracycline (10 μg/mL), X-gal (100 μg/mL), and IPTG (50 μg/mL), and subjected to standing culture at 37° C. for 24 hours (until presence or absence of coloring of the colony (either blue or white) was determined).

(9) A white colony was picked up with a platinum loop and inoculated on a new LB plate (similar to the above) and subjected to standing culture at 37° C. overnight. Thereafter, coloring was again checked.

(10) *Escherichia coli* (DH5α) derived from the white colony checked again in (9) above was inoculated on a 5 mL of an LB liquid culture medium containing kanamycin (50 μg/mL), gentamicin (7 μg/mL), and tetracycline (10 μg/mL), and subjected to shake culture at 37° C. overnight.

(11) W-MVP cloned Bacmid was purified from *Escherichia coli* (DH10Bac) cultured overnight, with QIAprep Spin Miniprep Kit of QIAGEN. Since Bacmid has a very large size, in purification, an elution buffer heated to 70° C. was used.

[B] Multiplication of W-MVP Cloned Recombinant Baculovirus (Production of Virus Solution)

A procedure below was performed in a safety cabinet.

(1) A concentration of 519 cells (1.5-2.0×10$^6$ cells/mL) being cultured in an Sf900-II culture medium (containing 10% serum) of Invitrogen was prepared to 1.2×10$^5$ cells/mL by being diluted with an Sf900-II culture medium (containing 10% serum) in a 15-mL tube.

(2) In a 12-well culture plate, 1 mL of a cell culture solution prepared to a final concentration of 0.4×10$^5$ cells/mL was introduced. Three hundred microliters of the culture solution at 1.2×10$^5$ cells/mL described above and 700 μL of the Sf900-II culture medium (containing 10% serum) were added to obtain a volume of 1 mL in total.

(3) The cells were attached to a bottom surface of the cell culture plate by resting them at 27° C. for 20 minutes.

(4) In a 1.5-mL tube, 214 μL of Grace medium unsupplement, 8 μL of Cellfectin, and 1 μg of Bacmid were mixed and left at a room temperature for 30 minutes in the safety cabinet (Cellfectin was used after being stirred for approximately 10 seconds with a vortex mixer).

(5) The 12-well culture plate in (3) above was observed with an inverted microscope and attachment of the cells onto the bottom surface of a container was confirmed. Then, the culture medium was removed (suctioned with a pipetman while the plate was inclined toward the back and the lid was placed as standing in the front).

(6) After the culture medium was removed, the cells were washed with 1 mL of Grace medium unsupplement. A cleaning solution was discarded.

(7) Thereafter, a solution mixture of Bacmid and Cellfectin described above was poured over the cells.

(8) The 12-well plate was placed in a sealed Tupperware® and was rested at 27° C. for 4 hours. In order to maintain a humidity in the Tupperware®, several sheets of Kimwipe™ wetted with pure water and 1 mL of 0.5M EDTA were placed in a corner of the Tupperware®.

(9) After 4 hours, 400 μL of Grace medium unsupplement (containing 10% serum) was layered and cultured at 27° C. for two days.

(10) After culturing for two days, the culture solution was transferred to a 1.5-mL tube, and the cells were precipitated by high-speed centrifugation (4,000×g, 3 min.). Since a supernatant was a virus solution (P0), the supernatant was transferred to a new 1.5-mL tube. The virus solution (P0) was stored in a chromatography chamber at 4° C. having a light-shielding film put thereon.

(11) A culture solution was added to a culture flask having an area of base of 25 cm$^2$ such that the number of cells was 3×10$^6$ cells (the volume of the solution was 5 mL in total). For example, in a case that the number of Sf9 cells being cultured in the Sf900-II culture medium (containing 10% serum) was 1×10$^6$ cells/mL, a solution of 5 mL which was obtained by adding 2 mL of the 51900-II culture medium (containing 10% serum) to 3 mL of the culture solution was introduced in the culture flask.

(12) The cells were attached to the bottom surface of the cell culture flask by resting them at 27° C. for 15 minutes.

(13) Two hundred microliters of the P0 virus solution were added and cultured for three days.

(14) After culturing for three days and before collection of a virus solution (P1), a culture solution was added to a culture flask having an area of base of 75 cm$^2$ such that the number of cells was 9×10$^6$ cells (the volume of the solution was 15 mL in total). By preparing 15 mL of the culture solution at 6×10$^5$ cells/mL, the total number of cells was 9×10$^6$ cells.

(15) The cells were attached to the bottom surface of the cell culture flask by resting them at 27° C. for 15 minutes.

(16) Before collection of the virus solution (P1), 0.5 mL of a supernatant was taken out of the culture flask having an area of base of 25 cm$^2$ described above with the use of a pipet, and added to the culture solution in (14) above (for prevention of contamination). Thereafter, the culture solution was cultured at 27° C. for three days.

(17) While the remaining culture solution was suctioned and discharged by the pipet, the cells attached to the bottom surface of the flask were removed and transferred to a 15-mL tube and precipitated by high-speed centrifugation (4,000×g, 3 min.). Since the supernatant was the virus solution (P1), the supernatant was transferred to a new 15-mL tube. The Sf9 cells which fell as the precipitate were subjected to freeze preservation at −80° C. for checking expression. The virus solution (P1) was stored in a chromatography chamber at 4° C. having a light-shielding film put thereon.

(18) After culturing for three days in the culture flask having an area of base of 75 cm$^2$, while the culture solution was suctioned and discharged by a pipet, the cells attached to the bottom surface of the flask were removed and transferred to a 50-mL tube and precipitated by high-speed centrifugation (4,000×g, 3 min.). Since a supernatant was a virus solution (P2), the supernatant was transferred to a new 50-mL tube. The Sf9 cells which fell as the precipitate were subjected to freeze preservation at −80° C. for checking expression. The virus solution (P2) was stored in a chromatography chamber at 4° C. having a light-shielding film put thereon.

(19) Thirty milliliters of a culture solution at 1×10$^6$ cells/mL were prepared in a 1-L spinner flask, 3 mL (a quantity equivalent to 1% of a culture medium) of the virus solution (P2) was added, and the resultant product was cultured at 27° C. for three days.

(20) After culturing for three days, the culture solution was transferred to a centrifugal tube and the cells were precipitated by high-speed centrifugation (4,000×g, 30 min.). Since a supernatant was a virus solution (P3), the supernatant was transferred to a new 500-mL medium bottle. The centrifugal tube, a lid of the centrifugal tube, and the medium bottle used here had been sterilized by autoclaving as being wrapped in an aluminum foil. The 519 cells which fell as the precipitate were subjected to freeze preservation at −80° C. for purification. The virus solution (P3) was stored in a chromatography chamber at 4° C. having a light-shielding film put thereon.

(21) Five hundred milliliters of the culture solution at 1×10$^6$ cells/mL were prepared in a 3-L spinner flask, 5 mL (a quantity equivalent to 1% of a culture medium) of the virus solution (P3) was added, and the resultant product was cultured at 27° C. for three days.

(22) After culturing for three days, the culture solution was transferred to a centrifugal tube and the cells were precipitated by high-speed centrifugation (4,000×g, 30 min.). Since a supernatant was a virus solution (P4), the supernatant was transferred to a new 500-mL medium bottle. The centrifugal tube, a lid of the centrifugal tube, and the medium bottle used here had been sterilized by autoclaving as being wrapped in an aluminum foil. The Sf9 cells which fell as the precipitate were subjected to freeze preservation at −80° C. for purification. The virus solution (P4) was stored in a chromatography chamber at 4° C. having a light-shielding film put thereon.

[2] Construction Using Insect Cells, of Abundant Expression System of MVP (LZ-MVP) Having Leucine Zipper Added to N Terminal An operation was performed in a procedure below.

(1) A DNA (a leucine zipper gene) (containing restriction enzyme sites of BamHI and EcoRI) (SEQ ID NO: 2) (an amino acid sequence of the expressed leucine zipper shown in SEQ ID NO: 3) encoding 249th arginine to 281th arginine in an amino acid sequence (SEQ ID NO: 1) of yeast-derived GCN4 (281 amino acid) was introduced in a pGEM-T vector of Promega KK, and leucine zipper-cloned plasmid was purified with the use of QIAprep Spin Miniprep Kit of QIAGEN. A base sequence of the leucine zipper gene introduced in pFastBac (containing a restriction enzyme site (BamHI, EcoRI) and starting Met) is shown in SEQ ID NO: 4 and an amino acid sequence of the expressed leucine zipper is shown in SEQ ID NO: 5.

(2) The leucine zipper gene was cut from the pGEM-T vector by using restriction enzymes BamHI and EcoRI.

(3) Similarly, pFastBac cloned with a rat derived W-MVP was also treated with restriction enzymes BamHI and EcoRI.

(4) A fragment of the leucine zipper gene and a fragment of the MVP gene obtained in (2) and (3) above were subjected to agarose gel electrophoresis, a target band was cut, and a target product was purified from the gel with the use of QIAquick Gel Extraction Kit of Qiagen.

(5) The both fragments purified in (4) above were ligated with the use of DNA Ligation Kit (Mighty Mix) of Takara Bio Inc. (a base sequence after ligation is shown in SEQ ID NO: 6 and amino acid sequences of an expressed leucine zipper and an MVP are shown in SEQ ID NOs: 7 and 8).

(6) An operation the same as in preparation of a W-MVP cloned recombinant Baculovirus genome (the procedures (1) to (11)) and multiplication of the W-MVP cloned recombinant baculovirus (the procedures (1) to (20)) described above was performed to multiply LZ-MVP cloned recombinant baculoviruses, to prepare a virus solution (P4).

[3] Insertion of Glycine Linker Between Leucine Zipper of LZ-MVP and MVP

In the constructed expression system above, a site of EcoRI (GAATTC) remained between a leucine zipper gene and an MVP gene, and may inhibit formation of a vault particle. Therefore, the present inventor substituted these with a Gly linker which was a series of 3 residues of an amino acid (glycine (Gly)) having a smallest side chain of which amino acid sequence is shown in SEQ ID NO: 9) or 6 residues (Gly6) (of which amino acid sequence is shown in SEQ ID NO: 10).

(1) The following three types of primers were made (a base sequence encoding Gly is gcc).

```
forward primer (lzmvp_0g_f)
                                        (SEQ ID NO: 11)
atggcaactgaagaggccat forward primer (lzmvp_3g_f)
                                        (SEQ ID NO: 12)
ggcggcggcatggcaactgaagaggccatcatccgcatc reverse primer (lzmvp_3g_r)
                                        (SEQ ID NO: 13)
GCCAGATTAAAGAAATTAGTTGGCGAACGCggcggcggc
```

A complementary sequence of a reverse primer is as follows.

```
                                        (SEQ ID NO: 14)
gccgccgccgcgttcgccaactaatttctttaatctggc
```

(2) When a linker formed of the Gly3 residues was inserted, lzmvp_0g_f and lzmvp_3_g_r were used as primers, and when a linker formed of the Gly6 residues was inserted, lzmvp_3g_f and lzmvp_3g_r were used as primers. With pFastBac of an earlier made LZ-MVP being used as a template, PCR (2 minutes at 94° C.→10 seconds at 98° C.→8 minutes at 68° C. (an underlined part being performed 10 cycles)) was carried out with the use of KOD-plus Mutagenesis kit manufactured by Toyobo Co., Ltd.

(3) After PCR, DpnI included in KOD-plus Mutagenesis kit manufactured by Toyobo Col, Ltd. was used to digest a template plasmid. In a 1.5-mL tube, 50 μL of a PCR product and 2 μL of DpnI were mixed, tapped and spun down, and thereafter incubated at 37° C. for 1 hour.

(4) In a 1.5-mL tube, 2 μL of a reaction solution in (3) above, 7 μL of sterilized water, 5 μL of Ligation high, and 1 μL of T4 polynucleotide kinase were added in this order, tapped and spun down, and thereafter incubated at 16° C. for 1 hour.

(5) Five microliters of the reaction solution in (4) above were added to 50 μL of *Escherichia coli* DH5α and rested on ice for 30 minutes.

(6) Heat shock was provided at 42° C. for 45 seconds.

(7) The solution was rested on ice for 2 minutes.

(8) Four hundred and fifty microliters of an SOC culture medium were added and subjected to shake culture at 37° C. for 1 hour.

(9) Fifty microliters of the culture solution in (8) above were poured over an LB plate containing Ampicillin (100 μg/mL).

(10) The plate was subjected to standing culture at 37° C. overnight.

Henceforth, an operation the same as in the procedures (2) to (20) for preparation of a W-MVP cloned recombinant baculovirus genome described above was performed to make a virus solution (P4) of LZMVP in which a Gly linker had been introduced between a leucine zipper and an MVP (LZMVP_Gly3, LZMVP_Gly6).

[4] Purification of Vault (W-Vault, LZ-Vault)

(1) In a 3-L spinner flask, 500 mL of Sf9 cells was cultured, and P4 or P3 virus solution was added for infection at the time point when the number of cells attained to 1×10$^6$ cells/mL, and cultured for three days.

(2) After culturing for three days, the culture solution was transferred to a centrifugal tube and the cells were precipitated by high-speed centrifugation (4,000×g, 30 min.).

(3) The precipitated cells were suspended in a PBS Buffer, and the suspension was transferred to a centrifugal tube and subjected to high-speed centrifugation (4,000×g, 30 min.). Thus, the cells were washed to remove medium components.

(4) The cells obtained as the precipitate were suspended in 100 mL of Buffer A for cell disruption (50 mM Tris-HCl (pH 7.5), 75 mM NaCl, 1.5 mM $MgCl_2$, 1 mM DTT, 1 mM PMSF, and two protease inhibitors for animal cells (manufactured by Nacalai Tesque, Inc.)), and subjected to ultrasonic disruption (TOMY UD-201, OUTPUT 2, DUTY 60, 2 min.×2).

(5) A homogenate was subjected to high-speed centrifugation at 14,300 rpm for 30 minutes at 4° C. with the use of a high-speed centrifuge (Beckman HP-26XP, JA25.50 rotor), and deposits resulting from cell disruption were removed as the precipitate.

(6) A supernatant was subjected to ultra-high-speed centrifugation at 40,000 rpm for 2 hours at 4° C. with the use of an ultra-high-speed centrifuge (Hitachi CP80WX, P45AT rotor), to thereby shed a vault fraction as a precipitate.

(7) A small amount of Buffer A for purification (50 mM Tris-HCl (pH 7.5), 75 mM NaCl, 1.5 mM $MgCl_2$, 1 mM DTT, and 1 mM PMSF) was added to the vault fraction obtained as the precipitate, and the vault fraction was suspended with a Dounce homogenizer.

(8) To the solution in (7) above, equal parts of Ficoll/Sucrose Buffer (90 mM MES-NaOH (pH 6.5), 10 mM Sodium phosphate, 1 mM $MgCl_2$, 0.5 mM EGTA, 0.02% $NaN_3$, 14% Ficoll-PM70, and 14% Sucrose) were added and mixed well.

(9) The solution in (8) above was subjected to ultra-high-speed centrifugation at 25,200 rpm for 10 minutes at 4° C. with the use of an ultra-high-speed centrifuge (Hitachi CP80WX, P45AT rotor), to thereby shed an unwanted substance as a precipitate.

(10) A vault fraction of the supernatant was four-fold diluted with Buffer A for purification, and subjected to ultra-high-speed centrifugation at 40,000 rpm for 2 hours at 4° C. with the use of an ultra-high-speed centrifuge (Hitachi CP80WX, P45AT rotor), to thereby shed a vault fraction as a precipitate.

(11) A small amount of Buffer A for purification was added to the vault fraction obtained as the precipitate and the vault fraction was suspended with a Dounce homogenizer.

(12) A density gradient of sucrose was created in a centrifugal tube of the ultra-high-speed centrifuge (Hitachi CP80WX, P28S rotor). From the bottom of the centrifugal tube, 4 mL of 60% Sucrose, 5 mL of 50% Sucrose, 5 mL of 45% Sucrose, 5 mL of 40% Sucrose, 5 mL of 30% Sucrose, and 5 mL of 20% Sucrose were layered. Four such tubes were created.

(13) Five milliliters of the solution in (11) above were layered on a 20% layer of the density gradient of sucrose in (12) above.

(14) Ultra-high centrifugation was carried out at 25,000 rpm for 16 hours at 4° C. with the use of an ultra-high-speed centrifuge (Hitachi CP80WX, P28S rotor).

(15) Since vaults were contained in a part of 40-45% fractions and a 50% fraction, they were collected with a pipet. The 40 and 45% fractions were collected totally (5 mL each) and half of the 50% fraction (2.5 mL) was collected.

(16) The solution collected in (15) above was four-fold diluted with Buffer A for purification and subjected to ultra-high-speed centrifugation at 40,000 rpm for 2 hours at 4° C. with the use of an ultra-high-speed centrifuge (Hitachi CP80WX, P45AT rotor), to thereby shed a vault fraction as a precipitate.

(17) A small amount of Buffer A was added to the vault fraction obtained as the precipitate and the vault fraction was suspended with a Dounce homogenizer.

(18) A vault sample in (17) above was filtered through a 0.22-μm filter to thereby remove debris.

(19) Two milliliters of the sample in (18) above were applied to a gel filtration column (manufactured by GE Healthcare Japan, Sephacryl S-500, 26/60) equilibrated by 2 bed volumes of Buffer A for gel filtration (50 mM Tris-HCl (pH 7.5), 75 mM NaCl, 1.5 mM $MgCl_2$, and 1 mM DTT), and the sample was fractionated by 4 mL at a flow rate of 0.5 mL/min.

(20) Since a target vault fraction comes out around 140 to 190 mL (fraction Nos. 39-49) after application of the sample, this vault fraction was collected and subjected to ultra-high-speed centrifugation at 40,000 rpm for 2 hours at 4° C. with the use of an ultra-high-speed centrifuge (Hitachi CP80WX, P45AT rotor), to thereby shed a vault fraction as a precipitate. (Around 90 to 110 mL (fraction Nos. 27-30), an aggregate of vaults comes out. Therefore, uniform vault particles can be obtained by removing the aggregate).

(21) A small amount of Buffer A was added to the vault fraction obtained as the precipitate and the vault fraction was suspended with a Dounce homogenizer, which was adopted as a final purified preparation.

Figure 6:
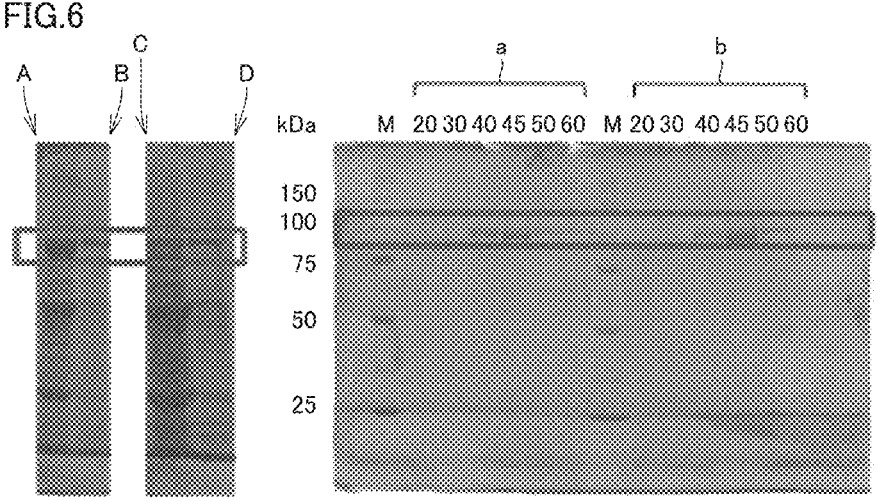
FIG. 6 shows on the left, a photograph showing results of SDS-PAGE after disruption and showings a supernatant (a lane A) and a precipitate (a lane B) of LZMVP_Gly3 and a supernatant (a lane C) and a precipitate (a lane D) of LZMVP_Gly6, and shows on the right, a photograph showing results of SDS-PAGE after sucrose density gradient centrifugation, in which a group a on the left shows results of LZMVP_Gly3 and a group b on the right shows results of LZMVP_Gly6.
Figure 7:
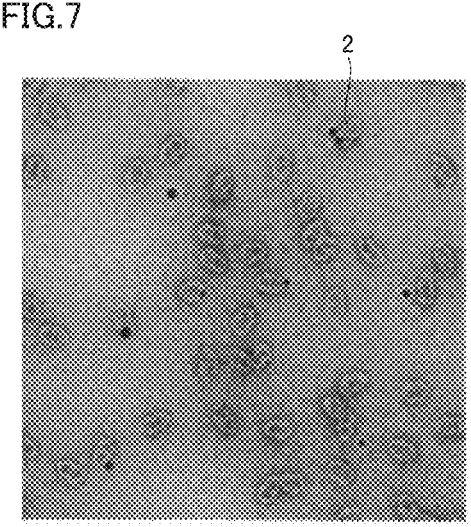
FIG. 7 shows an electron micrograph showing a final purified preparation of LZMVP_Gly3.

FIG. 6 shows on the left, a photograph showing results of SDS-PAGE after disruption (the procedure (9) above) and showing a supernatant (a lane A) and a precipitate (a lane B) of LZMVP_Gly3 and a supernatant (a lane C) and a precipitate (a lane D) of LZMVP_Gly6. FIG. 6 shows on the right, a photograph showing results of SDS-PAGE after sucrose density gradient centrifugation (the procedure (14) above), in which a group a on the left shows results of LZMVP_Gly3 and a group b on the right shows results of LZMVP_Gly6. FIG. 7 shows an electron micrograph showing a final purified preparation of LZMVP_Gly3.

[5] Quantification of Protein of Purified Vault (1) Quantification of proteins of W-MVP, LZMVP_Gly3, and LZMVP_Gly6 obtained as described above was carried out with the use of BCA Protein Assay Reagent Kit of Pierce.

(2) In a 15-mL tube, 5 mL of a reagent A of the kit and 100 μL of a reagent B were introduced and mixed well.

(3) Seven tubes each obtained by introducing 500 μL of the solution mixture in (2) above in a 1.5 mL Eppendorf tube were prepared.

(4) Twenty five microliters of each of 5 BSA standard solutions (1000, 500, 250, 125, and 62.5 μg/ml) prepared in advance were taken, introduced in the 1.5-mL tube in (3) above, and mixed well in a vortex mixer.

(5) Two types of solutions each obtained by diluting a vault solution to be quantified (containing W-MVP, LZMVP_Gly3, or LZMVP_Gly6) with ultrapure water were prepared (for example, 5-fold dilution and 10-fold dilution, or 25-fold dilution and 50-fold dilution).

(6) The two types of the diluted vault solutions fabricated in (5) above were each introduced in the 1.5 mL tube in (3) above and mixed well in a vortex mixer.

(7) The 1.5-mL tubes in (4) above and (6) above were incubated at 37° C. for 30 minutes.

(8) An absorbance of (7) above at 562 nm was measured with a spectrophotometer (colorimetric analysis based on coordination of reduced Cu (+) and bicinchoninic acid (BCA) resulting from Biuret test).

(9) Initially, measurement results of BCA were plotted with the ordinate representing an absorbance and the abscissa representing a BSA concentration, and an approximate curve (a standard curve) was found with the method of least squares.

(10) A concentration of the vault diluted solution was found from the standard curve in (9) above and then a concentration of a vault undiluted solution was found from a dilution factor.

(11) The concentration of the vault undiluted solution was multiplied with a total fluid volume, to thereby calculate total yields of vaults.

(12) Consequently, a W-vault (Comparative Example 1) weighed 3 to 5 mg per 1 L culture, whereas yields from 70 to 80 mg exceeding approximately 10 times were achieved with an LZ-vault (LZMVP_Gly3 (Example 1) and LZMVP_Gly6 (Example 2)).

It should be understood that the embodiments and the experimental examples disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST

1 artificial bioparticle; 2 vault; 3 MVP; 4 leucine zipper; 5 cap; 6 shoulder; 7 body; 8 waist; 9 cap helix; 10 cap ring; 11 drug; 12 antigen; 13 target cell; and 14 endosome.

The invention claimed is:

1. An artificial bioparticle comprising multiple, self-assembling copies of Major Vault Protein (MVP), wherein a leucine zipper is fused to the N-terminus of each MVP via a linker comprising 3 to 6 glycines.

2. The artificial bioparticle according to claim 1, wherein the leucine zipper is derived from GCN4 which is a transcription activator factor of yeast.

3. A method of manufacturing the artificial bioparticle according to claim 1, comprising expressing a protein comprising a leucine zipper linked to the N-terminus of an MVP via a linker comprising 3 to 6 glycines.

4. The artificial bioparticle according to claim 1, wherein the linker consists of 3 to 6 glycines.

5. The artificial bioparticle according to claim 1, wherein the linker consists of 6 glycines.

* * * * *

SEQUENCE LISTING

```
<160> NUMBER OF SEQ ID NOS: 14

<210> SEQ ID NO 1
<211> LENGTH: 281
<212> TYPE: PRT
<213> ORGANISM: Saccharomyces cerevisiae

<400> SEQUENCE: 1

Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
        115                 120                 125

Pro Val Thr Thr Asp Asp Val Ser Leu Ala Asp Lys Ala Ile Glu Ser
    130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
    210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255
```

```
Val Glu Glu Leu Leu Ser Lys Asn Tyr His Leu Glu Asn Glu Val Ala
            260                 265                 270

Arg Leu Lys Lys Leu Val Gly Glu Arg
        275                 280

<210> SEQ ID NO 2
<211> LENGTH: 102
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(102)

<400> SEQUENCE: 2 atg aga atg aaa caa ctt gaa gac aag gtt gaa gaa ttg ctt tcg aaa      48
Met Arg Met Lys Gln Leu Glu Asp Lys Val Glu Glu Leu Leu Ser Lys
1               5                   10                  15 aat tat cac ttg gaa aat gag gtt gcc aga tta aag aaa tta gtt ggc      96
Asn Tyr His Leu Glu Asn Glu Val Ala Arg Leu Lys Lys Leu Val Gly
            20                  25                  30 gaa cgc                                                              102
Glu Arg <210> SEQ ID NO 3
<211> LENGTH: 34
<212> TYPE: PRT
<213> ORGANISM: Artificial Sequence
<220> FEATURE:
<223> OTHER INFORMATION: Synthetic Sequence

<400> SEQUENCE: 3

Met Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg

<210> SEQ ID NO 4
<211> LENGTH: 114
<212> TYPE: DNA
<213> ORGANISM: Artificial Sequence
<220> FEATURE:
<223> OTHER INFORMATION: Synthetic Leucine Zipper Gene
<220> FEATURE:
<221> NAME/KEY: CDS
<222> LOCATION: (1)..(114)

<400> SEQUENCE: 4 gga tcc atg aga atg aaa caa ctt gaa gac aag gtt gaa gaa ttg ctt      48
Gly Ser Met Arg Met Lys Gln Leu Glu Asp Lys Val Glu Glu Leu Leu
1               5                   10                  15 tcg aaa aat tat cac ttg gaa aat gag gtt gcc aga tta aag aaa tta      96
Ser Lys Asn Tyr His Leu Glu Asn Glu Val Ala Arg Leu Lys Lys Leu
            20                  25                  30 gtt ggc gaa cgc gaa ttc                                              114
Val Gly Glu Arg Glu Phe
        35

<210> SEQ ID NO 5
<211> LENGTH: 38
<212> TYPE: PRT
<213> ORGANISM: Artificial Sequence
```

-continued

```
<220> FEATURE:
<223> OTHER INFORMATION: Synthetic Leucine Zipper Gene

<400> SEQUENCE: 5

Gly Ser Met Arg Met Lys Gln Leu Glu Asp Lys Val Glu Glu Leu Leu
1               5                   10                  15

Ser Lys Asn Tyr His Leu Glu Asn Glu Val Ala Arg Leu Lys Lys Leu
            20                  25                  30

Val Gly Glu Arg Glu Phe
        35

<210> SEQ ID NO 6
<211> LENGTH: 2700
<212> TYPE: DNA
<213> ORGANISM: Artificial Sequence
<220> FEATURE:
<223> OTHER INFORMATION: Synthetic Leucine Zipper and MVP
<220> FEATURE:
<221> NAME/KEY: CDS
<222> LOCATION: (7)..(108)
<220> FEATURE:
<221> NAME/KEY: CDS
<222> LOCATION: (115)..(2700)

<400> SEQUENCE: 6 ggatcc atg aga atg aaa caa ctt gaa gac aag gtt gaa gaa ttg ctt      48
       Met Arg Met Lys Gln Leu Glu Asp Lys Val Glu Glu Leu Leu
       1               5                   10 tcg aaa aat tat cac ttg gaa aat gag gtt gcc aga tta aag aaa tta     96
Ser Lys Asn Tyr His Leu Glu Asn Glu Val Ala Arg Leu Lys Lys Leu
15                  20                  25                  30 gtt ggc gaa cgc gaattc atg gca act gaa gag gcc atc atc cgc atc    144
Val Gly Glu Arg        Met Ala Thr Glu Glu Ala Ile Ile Arg Ile
                       35                  40 ccc cca tac cac tac atc cat gtg ctg gac cag aac agt aat gtg tcc   192
Pro Pro Tyr His Tyr Ile His Val Leu Asp Gln Asn Ser Asn Val Ser
45                  50                  55                  60 cgt gtg gag gtt gga cca aag acc tac atc cgg cag gac aat gag agg   240
Arg Val Glu Val Gly Pro Lys Thr Tyr Ile Arg Gln Asp Asn Glu Arg
                65                  70                  75 gta ctg ttt gcc cca gtt cgc atg gtg acc gtc ccc cca cgc cac tac   288
Val Leu Phe Ala Pro Val Arg Met Val Thr Val Pro Pro Arg His Tyr
            80                  85                  90 tgc ata gtg gcc aac cct gtg tcc cgg gac acc cag agt tct gtg tta   336
Cys Ile Val Ala Asn Pro Val Ser Arg Asp Thr Gln Ser Ser Val Leu
                95                 100                 105 ttt gac atc aca gga caa gtc cga ctc cgg cac gct gac cag gag atc   384
Phe Asp Ile Thr Gly Gln Val Arg Leu Arg His Ala Asp Gln Glu Ile
            110                 115                 120 cga cta gcc cag gac ccc ttc ccc ctg tat cca ggg gag gtg ctg gaa   432
Arg Leu Ala Gln Asp Pro Phe Pro Leu Tyr Pro Gly Glu Val Leu Glu
125                 130                 135                 140 aag gac atc acc cca ctg cag gtg gtt ctg ccc aac aca gca ctg cat   480
Lys Asp Ile Thr Pro Leu Gln Val Val Leu Pro Asn Thr Ala Leu His
                145                 150                 155 ctt aag gcg ttg ctg gac ttt gag gat aag aat gga gac aag gtc atg   528
Leu Lys Ala Leu Leu Asp Phe Glu Asp Lys Asn Gly Asp Lys Val Met
            160                 165                 170 gca gga gac gag tgg cta ttt gag gga cct ggc acc tac atc cca cag   576
Ala Gly Asp Glu Trp Leu Phe Glu Gly Pro Gly Thr Tyr Ile Pro Gln
        175                 180                 185 aag gaa gtg gaa gtc gtg gag atc att cag gcc aca gtc atc aaa cag   624
```

```
                Lys Glu Val Glu Val Glu Ile Ile Gln Ala Thr Val Ile Lys Gln
                    190                 195                 200 aac caa gca ctg cgg cta agg gcc cga aag gag tgc ttt gac cgg gag       672
Asn Gln Ala Leu Arg Leu Arg Ala Arg Lys Glu Cys Phe Asp Arg Glu
205                 210                 215                 220 ggc aag ggg cgc gtg aca ggt gag gag tgg ctg gtc cga tcc gtg ggg       720
Gly Lys Gly Arg Val Thr Gly Glu Glu Trp Leu Val Arg Ser Val Gly
                    225                 230                 235 gct tac ctc cca gct gtc ttt gaa gag gtg ctg gat ctg gtg gat gct       768
Ala Tyr Leu Pro Ala Val Phe Glu Glu Val Leu Asp Leu Val Asp Ala
                240                 245                 250 gtg atc ctt aca gaa aag act gcc ctg cac ctc cgg gct ctg cag aac       816
Val Ile Leu Thr Glu Lys Thr Ala Leu His Leu Arg Ala Leu Gln Asn
            255                 260                 265 ttc agg gac ctt cgg gga gtg ctc cac cgc acc ggg gag gaa tgg tta       864
Phe Arg Asp Leu Arg Gly Val Leu His Arg Thr Gly Glu Glu Trp Leu
        270                 275                 280 gtg aca gtg cag gac aca gaa gcc cat gtt cca gat gtc tat gag gag       912
Val Thr Val Gln Asp Thr Glu Ala His Val Pro Asp Val Tyr Glu Glu
285                 290                 295                 300 gtg ctt ggg gta gta ccc atc acc acc ctg gga cct cga cac tac tgt       960
Val Leu Gly Val Val Pro Ile Thr Thr Leu Gly Pro Arg His Tyr Cys
                    305                 310                 315 gtc att ctt gac cca atg gga cca gac ggc aag aac cag ctg gga caa      1008
Val Ile Leu Asp Pro Met Gly Pro Asp Gly Lys Asn Gln Leu Gly Gln
                320                 325                 330 aag cgt gtt gtc aag gga gag aag tcc ttt ttc ctc cag cca gga gag      1056
Lys Arg Val Val Lys Gly Glu Lys Ser Phe Phe Leu Gln Pro Gly Glu
            335                 340                 345 agg ctg gag cga ggc atc cag gat gtg tat gtg ctg tca gag cag cag      1104
Arg Leu Glu Arg Gly Ile Gln Asp Val Tyr Val Leu Ser Glu Gln Gln
        350                 355                 360 ggg ctg cta ctg aag gca ctg cag ccc ctg gag gag gga gag agc gag      1152
Gly Leu Leu Leu Lys Ala Leu Gln Pro Leu Glu Glu Gly Glu Ser Glu
365                 370                 375                 380 gag aag gtc tcc cat cag gcc gga gac tgc tgg ctc atc cgt ggg ccc      1200
Glu Lys Val Ser His Gln Ala Gly Asp Cys Trp Leu Ile Arg Gly Pro
                    385                 390                 395 ctg gag tat gtg cca tct gca aaa gtg gag gtg gtg gag gag cgt cag      1248
Leu Glu Tyr Val Pro Ser Ala Lys Val Glu Val Val Glu Glu Arg Gln
                400                 405                 410 gct atc cct ctg gac caa aat gag ggc atc tat gtg cag gat gtc aag      1296
Ala Ile Pro Leu Asp Gln Asn Glu Gly Ile Tyr Val Gln Asp Val Lys
            415                 420                 425 acg ggg aag gtg cgg gct gtg att gga agc acc tac atg ctg act cag      1344
Thr Gly Lys Val Arg Ala Val Ile Gly Ser Thr Tyr Met Leu Thr Gln
        430                 435                 440 gat gaa gtc ctg tgg gaa aag gag ctg cct tct ggg gtg gag gag ctg      1392
Asp Glu Val Leu Trp Glu Lys Glu Leu Pro Ser Gly Val Glu Glu Leu
445                 450                 455                 460 ctg aac ttg ggg cat gac cct ctg gca gac agg ggt cag aag ggc aca      1440
Leu Asn Leu Gly His Asp Pro Leu Ala Asp Arg Gly Gln Lys Gly Thr
                    465                 470                 475 gcc aag ccc ctt cag ccc tca gct cca agg aac aag acc cga gtg gtc      1488
Ala Lys Pro Leu Gln Pro Ser Ala Pro Arg Asn Lys Thr Arg Val Val
                480                 485                 490 agc tac cgt gtc ccg cac aat gca gcg gtg cag gtc tat gac tac aga      1536
Ser Tyr Arg Val Pro His Asn Ala Ala Val Gln Val Tyr Asp Tyr Arg
            495                 500                 505
```

```
                                                                     -continued gcc aag aga gcc cgt gtg gtc ttt ggg ccc gag cta gtg aca ctg gat      1584
Ala Lys Arg Ala Arg Val Val Phe Gly Pro Glu Leu Val Thr Leu Asp
    510             515                 520 cct gag gag cag ttc aca gta ttg tcc ctt tct gcc ggg cga ccc aag      1632
Pro Glu Glu Gln Phe Thr Val Leu Ser Leu Ser Ala Gly Arg Pro Lys
525             530                 535                 540 cgt cct cat gcc cgc cgt gca ctc tgc cta ctg gga cct gat ttc          1680
Arg Pro His Ala Arg Arg Ala Leu Cys Leu Leu Gly Pro Asp Phe
            545                 550                 555 ttt act gat gtc atc acc atc gaa act gca gat cat gcc agg ttg cag      1728
Phe Thr Asp Val Ile Thr Ile Glu Thr Ala Asp His Ala Arg Leu Gln
                560                 565                 570 ctg cag ctt gcc tac aac tgg cac ttt gaa ctg aag aac cgg aat gac      1776
Leu Gln Leu Ala Tyr Asn Trp His Phe Glu Leu Lys Asn Arg Asn Asp
            575                 580                 585 cct gca gag gca gcc aag ctt ttc tcc gtg cct gac ttc gtg ggt gac      1824
Pro Ala Glu Ala Ala Lys Leu Phe Ser Val Pro Asp Phe Val Gly Asp
        590                 595                 600 gcc tgc aag gcc att gca tcc cga gtc cgg ggg gct gta gcc tct gtc      1872
Ala Cys Lys Ala Ile Ala Ser Arg Val Arg Gly Ala Val Ala Ser Val
605                 610                 615                 620 acc ttt gat gac ttc cat aaa aac tca gcc cgg atc att cga atg gct      1920
Thr Phe Asp Asp Phe His Lys Asn Ser Ala Arg Ile Ile Arg Met Ala
                625                 630                 635 gtt ttt ggc ttt gag atg tct gaa gac aca ggt cct gat ggc aca ctc      1968
Val Phe Gly Phe Glu Met Ser Glu Asp Thr Gly Pro Asp Gly Thr Leu
            640                 645                 650 ctg ccc aag gct cga gac cag gca gtc ttt ccc caa aac ggg ctg gta      2016
Leu Pro Lys Ala Arg Asp Gln Ala Val Phe Pro Gln Asn Gly Leu Val
        655                 660                 665 gtc agc agt gtg gat gtg cag tca gtg gag ccc gtg gac cag agg acc      2064
Val Ser Ser Val Asp Val Gln Ser Val Glu Pro Val Asp Gln Arg Thr
    670                 675                 680 cgg gat gcc ctt cag cgc agc gtt cag ctg gcc atc gaa att acc acc      2112
Arg Asp Ala Leu Gln Arg Ser Val Gln Leu Ala Ile Glu Ile Thr Thr
685                 690                 695                 700 aac tcc cag gag gca gca gcc aag cac gag gct cag aga ctg gaa cag      2160
Asn Ser Gln Glu Ala Ala Ala Lys His Glu Ala Gln Arg Leu Glu Gln
                705                 710                 715 gaa gcc cgt ggt cgg ctt gag agg cag aag atc ttg gac cag tca gaa      2208
Glu Ala Arg Gly Arg Leu Glu Arg Gln Lys Ile Leu Asp Gln Ser Glu
            720                 725                 730 gct gaa aaa gcc cgc aag gaa ctc ttg gag ctt gag gct atg agc atg      2256
Ala Glu Lys Ala Arg Lys Glu Leu Leu Glu Leu Glu Ala Met Ser Met
        735                 740                 745 gct gtg gag agc acg ggt aat gcc aaa gca gag gct gag tcc cgt gca      2304
Ala Val Glu Ser Thr Gly Asn Ala Lys Ala Glu Ala Glu Ser Arg Ala
    750                 755                 760 gag gca gcg agg atc gaa gga gaa ggc tct gtg ctg cag gcc aag ctc      2352
Glu Ala Ala Arg Ile Glu Gly Glu Gly Ser Val Leu Gln Ala Lys Leu
765                 770                 775                 780 aag gca cag gcg cta gcc att gag acg gag gct gag ttg gag cga gta      2400
Lys Ala Gln Ala Leu Ala Ile Glu Thr Glu Ala Glu Leu Glu Arg Val
                785                 790                 795 aag aaa gta cga gag atg gaa ctg atc tat gcc cgg gcc cag ttg gag      2448
Lys Lys Val Arg Glu Met Glu Leu Ile Tyr Ala Arg Ala Gln Leu Glu
            800                 805                 810 ctg gag gtg agc aag gcg cag cag ctt gcc aat gtg gag gca aag aag      2496
Leu Glu Val Ser Lys Ala Gln Gln Leu Ala Asn Val Glu Ala Lys Lys
        815                 820                 825
```

-continued

```
ttc aag gag atg aca gag gca ctg ggc ccc ggc acc atc agg gac ctg    2544
Phe Lys Glu Met Thr Glu Ala Leu Gly Pro Gly Thr Ile Arg Asp Leu
    830                 835                 840 gct gtg gcc ggg cca gag atg cag gtg aaa ctt ctc cag tcc ctg ggc    2592
Ala Val Ala Gly Pro Glu Met Gln Val Lys Leu Leu Gln Ser Leu Gly
845                 850                 855                 860 ctg aaa tcc act ctc atc acc gat ggc tcg tct ccc atc aac ctc ttc    2640
Leu Lys Ser Thr Leu Ile Thr Asp Gly Ser Ser Pro Ile Asn Leu Phe
                865                 870                 875 agc aca gcc ttc ggg ttg ctg ggg ctg ggg tct gat ggt cag ccg cca    2688
Ser Thr Ala Phe Gly Leu Leu Gly Leu Gly Ser Asp Gly Gln Pro Pro
            880                 885                 890 gca cag aag tga                                                    2700
Ala Gln Lys
    895
```

<210> SEQ ID NO 7
<211> LENGTH: 34
<212> TYPE: PRT
<213> ORGANISM: Artificial Sequence
<220> FEATURE:
<223> OTHER INFORMATION: Synthetic Leucine Zipper and MVP

<400> SEQUENCE: 7

```
Met Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg
```

<210> SEQ ID NO 8
<211> LENGTH: 861
<212> TYPE: PRT
<213> ORGANISM: Artificial Sequence
<220> FEATURE:
<223> OTHER INFORMATION: Synthetic Leucine Zipper and MVP

<400> SEQUENCE: 8

```
Met Ala Thr Glu Glu Ala Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Val
        35                  40                  45

Arg Met Val Thr Val Pro Pro Arg His Tyr Cys Ile Val Ala Asn Pro
50                  55                  60

Val Ser Arg Asp Thr Gln Ser Ser Val Leu Phe Asp Ile Thr Gly Gln
65                  70                  75                  80

Val Arg Leu Arg His Ala Asp Gln Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asn Gly Asp Lys Val Met Ala Gly Asp Glu Trp Leu
    130                 135                 140

Phe Glu Gly Pro Gly Thr Tyr Ile Pro Gln Lys Glu Val Glu Val Val
145                 150                 155                 160
```

-continued

```
Glu Ile Ile Gln Ala Thr Val Ile Lys Gln Asn Gln Ala Leu Arg Leu
            165                 170                 175

Arg Ala Arg Lys Glu Cys Phe Asp Arg Glu Gly Lys Gly Arg Val Thr
        180                 185                 190

Gly Glu Glu Trp Leu Val Arg Ser Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Leu Gln Asn Phe Arg Asp Leu Arg Gly
225                 230                 235                 240

Val Leu His Arg Thr Gly Glu Glu Trp Leu Val Thr Val Gln Asp Thr
                245                 250                 255

Glu Ala His Val Pro Asp Val Tyr Glu Glu Val Leu Gly Val Val Pro
            260                 265                 270

Ile Thr Thr Leu Gly Pro Arg His Tyr Cys Val Ile Leu Asp Pro Met
        275                 280                 285

Gly Pro Asp Gly Lys Asn Gln Leu Gly Gln Lys Arg Val Val Lys Gly
    290                 295                 300

Glu Lys Ser Phe Phe Leu Gln Pro Gly Glu Arg Leu Glu Arg Gly Ile
305                 310                 315                 320

Gln Asp Val Tyr Val Leu Ser Glu Gln Gly Leu Leu Lys Ala
                325                 330                 335

Leu Gln Pro Leu Glu Glu Gly Glu Ser Glu Glu Lys Val Ser His Gln
                340                 345                 350

Ala Gly Asp Cys Trp Leu Ile Arg Gly Pro Leu Glu Tyr Val Pro Ser
            355                 360                 365

Ala Lys Val Glu Val Val Glu Glu Arg Gln Ala Ile Pro Leu Asp Gln
        370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Ser Gly Val Glu Glu Leu Leu Asn Leu Gly His Asp
            420                 425                 430

Pro Leu Ala Asp Arg Gly Gln Lys Gly Thr Ala Lys Pro Leu Gln Pro
        435                 440                 445

Ser Ala Pro Arg Asn Lys Thr Arg Val Val Ser Tyr Arg Val Pro His
    450                 455                 460

Asn Ala Ala Val Gln Val Tyr Asp Tyr Arg Ala Lys Arg Ala Arg Val
465                 470                 475                 480

Val Phe Gly Pro Glu Leu Val Thr Leu Asp Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Leu Lys Asn Arg Asn Asp Pro Ala Glu Ala Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
```

```
                    580                 585                 590
Lys Asn Ser Ala Arg Ile Ile Arg Met Ala Val Phe Gly Phe Glu Met
            595                 600                 605

Ser Glu Asp Thr Gly Pro Asp Gly Thr Leu Leu Pro Lys Ala Arg Asp
        610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700

Glu Leu Glu Leu Glu Ala Met Ser Met Ala Val Glu Ser Thr Gly
705                 710                 715                 720

Asn Ala Lys Ala Glu Ala Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Glu Arg Val Lys Val Arg Glu Met
        755                 760                 765

Glu Leu Ile Tyr Ala Arg Ala Gln Leu Glu Leu Glu Val Ser Lys Ala
    770                 775                 780

Gln Gln Leu Ala Asn Val Glu Ala Lys Lys Phe Lys Glu Met Thr Glu
785                 790                 795                 800

Ala Leu Gly Pro Gly Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Ser Pro Ile Asn Leu Phe Ser Thr Ala Phe Gly Leu
        835                 840                 845

Leu Gly Leu Gly Ser Asp Gly Gln Pro Pro Ala Gln Lys
    850                 855                 860

<210> SEQ ID NO 9
<211> LENGTH: 898
<212> TYPE: PRT
<213> ORGANISM: Artificial Sequence
<220> FEATURE:
<223> OTHER INFORMATION: Synthetic Sequence

<400> SEQUENCE: 9

Met Arg Met Lys Gln Leu Glu Asp Lys Val Glu Glu Leu Leu Ser Lys
1               5                  10                  15

Asn Tyr His Leu Glu Asn Glu Val Ala Arg Leu Lys Lys Leu Val Gly
                20                  25                  30

Glu Arg Gly Gly Gly Met Ala Thr Glu Glu Ala Ile Ile Arg Ile Pro
            35                  40                  45

Pro Tyr His Tyr Ile His Val Leu Asp Gln Asn Ser Asn Val Ser Arg
        50                  55                  60

Val Glu Val Gly Pro Lys Thr Tyr Ile Arg Gln Asp Asn Glu Arg Val
65                  70                  75                  80

Leu Phe Ala Pro Val Arg Met Val Thr Val Pro Pro Arg His Tyr Cys
```

```
                     85                  90                  95
Ile Val Ala Asn Pro Val Ser Arg Asp Thr Gln Ser Ser Val Leu Phe
                100                 105                 110
Asp Ile Thr Gly Gln Val Arg Leu Arg His Ala Asp Gln Glu Ile Arg
                115                 120                 125
Leu Ala Gln Asp Pro Phe Pro Leu Tyr Pro Gly Glu Val Leu Glu Lys
                130                 135                 140
Asp Ile Thr Pro Leu Gln Val Val Leu Pro Asn Thr Ala Leu His Leu
145                 150                 155                 160
Lys Ala Leu Leu Asp Phe Glu Asp Lys Asn Gly Asp Lys Val Met Ala
                165                 170                 175
Gly Asp Glu Trp Leu Phe Glu Gly Pro Gly Thr Tyr Ile Pro Gln Lys
                180                 185                 190
Glu Val Glu Val Val Glu Ile Ile Gln Ala Thr Val Ile Lys Gln Asn
                195                 200                 205
Gln Ala Leu Arg Leu Arg Ala Arg Lys Glu Cys Phe Asp Arg Glu Gly
                210                 215                 220
Lys Gly Arg Val Thr Gly Glu Glu Trp Leu Val Arg Ser Val Gly Ala
225                 230                 235                 240
Tyr Leu Pro Ala Val Phe Glu Glu Val Leu Asp Leu Val Asp Ala Val
                245                 250                 255
Ile Leu Thr Glu Lys Thr Ala Leu His Leu Arg Ala Leu Gln Asn Phe
                260                 265                 270
Arg Asp Leu Arg Gly Val Leu His Arg Thr Gly Glu Glu Trp Leu Val
                275                 280                 285
Thr Val Gln Asp Thr Glu Ala His Val Pro Asp Val Tyr Glu Glu Val
                290                 295                 300
Leu Gly Val Val Pro Ile Thr Thr Leu Gly Pro Arg His Tyr Cys Val
305                 310                 315                 320
Ile Leu Asp Pro Met Gly Pro Asp Gly Lys Asn Gln Leu Gly Gln Lys
                325                 330                 335
Arg Val Val Lys Gly Glu Lys Ser Phe Phe Leu Gln Pro Gly Glu Arg
                340                 345                 350
Leu Glu Arg Gly Ile Gln Asp Val Tyr Val Leu Ser Glu Gln Gln Gly
                355                 360                 365
Leu Leu Leu Lys Ala Leu Gln Pro Leu Glu Glu Gly Glu Ser Glu Glu
                370                 375                 380
Lys Val Ser His Gln Ala Gly Asp Cys Trp Leu Ile Arg Gly Pro Leu
385                 390                 395                 400
Glu Tyr Val Pro Ser Ala Lys Val Glu Val Val Glu Glu Arg Gln Ala
                405                 410                 415
Ile Pro Leu Asp Gln Asn Glu Gly Ile Tyr Val Gln Asp Val Lys Thr
                420                 425                 430
Gly Lys Val Arg Ala Val Ile Gly Ser Thr Tyr Met Leu Thr Gln Asp
                435                 440                 445
Glu Val Leu Trp Glu Lys Glu Leu Pro Ser Gly Val Glu Glu Leu Leu
                450                 455                 460
Asn Leu Gly His Asp Pro Leu Ala Asp Arg Gly Gln Lys Gly Thr Ala
465                 470                 475                 480
Lys Pro Leu Gln Pro Ser Ala Pro Arg Asn Lys Thr Arg Val Val Ser
                485                 490                 495
Tyr Arg Val Pro His Asn Ala Ala Val Gln Val Tyr Asp Tyr Arg Ala
                500                 505                 510
```

```
Lys Arg Ala Arg Val Val Phe Gly Pro Glu Leu Val Thr Leu Asp Pro
            515                 520                 525

Glu Glu Gln Phe Thr Val Leu Ser Leu Ser Ala Gly Arg Pro Lys Arg
530                 535                 540

Pro His Ala Arg Arg Ala Leu Cys Leu Leu Gly Pro Asp Phe Phe
545                 550                 555                 560

Thr Asp Val Ile Thr Ile Glu Thr Ala Asp His Ala Arg Leu Gln Leu
                565                 570                 575

Gln Leu Ala Tyr Asn Trp His Phe Glu Leu Lys Asn Arg Asn Asp Pro
            580                 585                 590

Ala Glu Ala Ala Lys Leu Phe Ser Val Pro Asp Phe Val Gly Asp Ala
        595                 600                 605

Cys Lys Ala Ile Ala Ser Arg Val Arg Gly Ala Val Ala Ser Val Thr
        610                 615                 620

Phe Asp Asp Phe His Lys Asn Ser Ala Arg Ile Ile Arg Met Ala Val
625                 630                 635                 640

Phe Gly Phe Glu Met Ser Glu Asp Thr Gly Pro Asp Gly Thr Leu Leu
                645                 650                 655

Pro Lys Ala Arg Asp Gln Ala Val Phe Pro Gln Asn Gly Leu Val Val
            660                 665                 670

Ser Ser Val Asp Val Gln Ser Val Glu Pro Val Asp Gln Arg Thr Arg
        675                 680                 685

Asp Ala Leu Gln Arg Ser Val Gln Leu Ala Ile Glu Ile Thr Thr Asn
        690                 695                 700

Ser Gln Glu Ala Ala Ala Lys His Glu Ala Gln Arg Leu Glu Gln Glu
705                 710                 715                 720

Ala Arg Gly Arg Leu Glu Arg Gln Lys Ile Leu Asp Gln Ser Glu Ala
                725                 730                 735

Glu Lys Ala Arg Lys Glu Leu Leu Glu Leu Glu Ala Met Ser Met Ala
            740                 745                 750

Val Glu Ser Thr Gly Asn Ala Lys Ala Glu Ala Glu Ser Arg Ala Glu
        755                 760                 765

Ala Ala Arg Ile Glu Gly Glu Gly Ser Val Leu Gln Ala Lys Leu Lys
        770                 775                 780

Ala Gln Ala Leu Ala Ile Glu Thr Glu Ala Glu Leu Glu Arg Val Lys
785                 790                 795                 800

Lys Val Arg Glu Met Glu Leu Ile Tyr Ala Arg Ala Gln Leu Glu Leu
                805                 810                 815

Glu Val Ser Lys Ala Gln Gln Leu Ala Asn Val Glu Ala Lys Lys Phe
            820                 825                 830

Lys Glu Met Thr Glu Ala Leu Gly Pro Gly Thr Ile Arg Asp Leu Ala
        835                 840                 845

Val Ala Gly Pro Glu Met Gln Val Lys Leu Leu Gln Ser Leu Gly Leu
        850                 855                 860

Lys Ser Thr Leu Ile Thr Asp Gly Ser Ser Pro Ile Asn Leu Phe Ser
865                 870                 875                 880

Thr Ala Phe Gly Leu Leu Gly Leu Gly Ser Asp Gly Gln Pro Pro Ala
                885                 890                 895

Gln Lys

<210> SEQ ID NO 10
<211> LENGTH: 901
<212> TYPE: PRT
```

<213> ORGANISM: Artificial Sequence
<220> FEATURE:
<223> OTHER INFORMATION: Synthetic Sequence

<400> SEQUENCE: 10

```
Met Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Gly Gly Gly Gly Gly Met Ala Thr Glu Glu Ala Ile Ile
        35                  40                  45

Arg Ile Pro Pro Tyr His Tyr Ile His Val Leu Asp Gln Asn Ser Asn
50                  55                  60

Val Ser Arg Val Glu Val Gly Pro Lys Thr Tyr Ile Arg Gln Asp Asn
65                  70                  75                  80

Glu Arg Val Leu Phe Ala Pro Val Arg Met Val Thr Val Pro Pro Arg
                85                  90                  95

His Tyr Cys Ile Val Ala Asn Pro Val Ser Arg Asp Thr Gln Ser Ser
            100                 105                 110

Val Leu Phe Asp Ile Thr Gly Gln Val Arg Leu Arg His Ala Asp Gln
        115                 120                 125

Glu Ile Arg Leu Ala Gln Asp Pro Phe Pro Leu Tyr Pro Gly Glu Val
130                 135                 140

Leu Glu Lys Asp Ile Thr Pro Leu Gln Val Val Leu Pro Asn Thr Ala
145                 150                 155                 160

Leu His Leu Lys Ala Leu Leu Asp Phe Glu Asp Lys Asn Gly Asp Lys
                165                 170                 175

Val Met Ala Gly Asp Glu Trp Leu Phe Glu Gly Pro Gly Thr Tyr Ile
            180                 185                 190

Pro Gln Lys Glu Val Glu Val Val Glu Ile Ile Gln Ala Thr Val Ile
        195                 200                 205

Lys Gln Asn Gln Ala Leu Arg Leu Arg Ala Arg Lys Glu Cys Phe Asp
210                 215                 220

Arg Glu Gly Lys Gly Arg Val Thr Gly Glu Glu Trp Leu Val Arg Ser
225                 230                 235                 240

Val Gly Ala Tyr Leu Pro Ala Val Phe Glu Glu Val Leu Asp Leu Val
                245                 250                 255

Asp Ala Val Ile Leu Thr Glu Lys Thr Ala Leu His Leu Arg Ala Leu
            260                 265                 270

Gln Asn Phe Arg Asp Leu Arg Gly Val Leu His Arg Thr Gly Glu Glu
        275                 280                 285

Trp Leu Val Thr Val Gln Asp Thr Glu Ala His Val Pro Asp Val Tyr
290                 295                 300

Glu Glu Val Leu Gly Val Val Pro Ile Thr Thr Leu Gly Pro Arg His
305                 310                 315                 320

Tyr Cys Val Ile Leu Asp Pro Met Gly Pro Asp Gly Lys Asn Gln Leu
                325                 330                 335

Gly Gln Lys Arg Val Val Lys Gly Glu Lys Ser Phe Phe Leu Gln Pro
            340                 345                 350

Gly Glu Arg Leu Glu Arg Gly Ile Gln Asp Val Tyr Val Leu Ser Glu
        355                 360                 365

Gln Gln Gly Leu Leu Leu Lys Ala Leu Gln Pro Leu Glu Glu Gly Glu
370                 375                 380

Ser Glu Glu Lys Val Ser His Gln Ala Gly Asp Cys Trp Leu Ile Arg
```

```
              385                 390                 395                 400
        Gly Pro Leu Glu Tyr Val Pro Ser Ala Lys Val Glu Val Glu
                        405                 410                 415

Arg Gln Ala Ile Pro Leu Asp Gln Asn Glu Gly Ile Tyr Val Gln Asp
                        420                 425                 430

Val Lys Thr Gly Lys Val Arg Ala Val Ile Gly Ser Thr Tyr Met Leu
                        435                 440                 445

Thr Gln Asp Glu Val Leu Trp Glu Lys Glu Leu Pro Ser Gly Val Glu
                        450                 455                 460

Glu Leu Leu Asn Leu Gly His Asp Pro Leu Ala Asp Arg Gly Gln Lys
        465                 470                 475                 480

Gly Thr Ala Lys Pro Leu Gln Pro Ser Ala Pro Arg Asn Lys Thr Arg
                        485                 490                 495

Val Val Ser Tyr Arg Val Pro His Asn Ala Ala Val Gln Val Tyr Asp
                        500                 505                 510

Tyr Arg Ala Lys Arg Ala Arg Val Val Phe Gly Pro Glu Leu Val Thr
                        515                 520                 525

Leu Asp Pro Glu Glu Gln Phe Thr Val Leu Ser Leu Ser Ala Gly Arg
        530                 535                 540

Pro Lys Arg Pro His Ala Arg Arg Ala Leu Cys Leu Leu Leu Gly Pro
        545                 550                 555                 560

Asp Phe Phe Thr Asp Val Ile Thr Ile Glu Thr Ala Asp His Ala Arg
                        565                 570                 575

Leu Gln Leu Gln Leu Ala Tyr Asn Trp His Phe Glu Leu Lys Asn Arg
                        580                 585                 590

Asn Asp Pro Ala Glu Ala Ala Lys Leu Phe Ser Val Pro Asp Phe Val
                        595                 600                 605

Gly Asp Ala Cys Lys Ala Ile Ala Ser Arg Val Arg Gly Ala Val Ala
                        610                 615                 620

Ser Val Thr Phe Asp Asp Phe His Lys Asn Ser Ala Arg Ile Ile Arg
        625                 630                 635                 640

Met Ala Val Phe Gly Phe Glu Met Ser Glu Asp Thr Gly Pro Asp Gly
                        645                 650                 655

Thr Leu Leu Pro Lys Ala Arg Asp Gln Ala Val Phe Pro Gln Asn Gly
                        660                 665                 670

Leu Val Val Ser Ser Val Asp Val Gln Ser Val Glu Pro Val Asp Gln
                        675                 680                 685

Arg Thr Arg Asp Ala Leu Gln Arg Ser Val Gln Leu Ala Ile Glu Ile
        690                 695                 700

Thr Thr Asn Ser Gln Glu Ala Ala Lys His Glu Ala Gln Arg Leu
        705                 710                 715                 720

Glu Gln Glu Ala Arg Gly Arg Leu Glu Arg Gln Lys Ile Leu Asp Gln
                        725                 730                 735

Ser Glu Ala Glu Lys Ala Arg Lys Glu Leu Leu Glu Leu Glu Ala Met
                        740                 745                 750

Ser Met Ala Val Glu Ser Thr Gly Asn Ala Lys Ala Glu Ala Glu Ser
                        755                 760                 765

Arg Ala Glu Ala Ala Arg Ile Glu Gly Glu Gly Ser Val Leu Gln Ala
                        770                 775                 780

Lys Leu Lys Ala Gln Ala Leu Ala Ile Glu Thr Glu Ala Glu Leu Glu
        785                 790                 795                 800

Arg Val Lys Lys Val Arg Glu Met Glu Leu Ile Tyr Ala Arg Ala Gln
                        805                 810                 815
```

```
Leu Glu Leu Glu Val Ser Lys Ala Gln Gln Leu Ala Asn Val Glu Ala
            820                 825                 830

Lys Lys Phe Lys Glu Met Thr Glu Ala Leu Gly Pro Gly Thr Ile Arg
        835                 840                 845

Asp Leu Ala Val Ala Gly Pro Glu Met Gln Val Lys Leu Leu Gln Ser
    850                 855                 860

Leu Gly Leu Lys Ser Thr Leu Ile Thr Asp Gly Ser Ser Pro Ile Asn
865                 870                 875                 880

Leu Phe Ser Thr Ala Phe Gly Leu Leu Gly Leu Gly Ser Asp Gly Gln
                885                 890                 895

Pro Pro Ala Gln Lys
            900

<210> SEQ ID NO 11
<211> LENGTH: 20
<212> TYPE: DNA
<213> ORGANISM: Artificial Sequence
<220> FEATURE:
<223> OTHER INFORMATION: Syntthetic Sequence

<400> SEQUENCE: 11
atggcaactg aagaggccat                                            20

<210> SEQ ID NO 12
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 12
ggcggcggca tggcaactga agaggccatc atccgcatc                       39

<210> SEQ ID NO 13
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 13
gccagattaa agaaattagt tggcgaacgc ggcggcggc                       39

<210> SEQ ID NO 14
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 14
gccgccgccg cgttcgccaa ctaatttctt taatctggc                       39
```